(12) United States Patent
Suzuki et al.

(10) Patent No.: US 7,955,252 B2
(45) Date of Patent: Jun. 7, 2011

(54) ENDOSCOPIC TREATMENT SYSTEM (75) Inventors: Keita Suzuki, Tokyo (JP); Keiichi Arai, Tokyo (JP); Hiroyoshi Watanabe, Hirosaki (JP); Tsutomu Okada, Tokyo (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 11/446,999

(22) Filed: Jun. 5, 2006

(65) Prior Publication Data
US 2006/0224162 A1 Oct. 5, 2006

Related U.S. Application Data (63) Continuation of application No. PCT/JP2005/006777, filed on Apr. 6, 2005.

(30) Foreign Application Priority Data

Apr. 15, 2004 (JP) .................................. 2004-119984

(51) Int. Cl.
A61B 1/00 (2006.01)
(52) U.S. Cl. ....................................... 600/106; 600/104
(58) Field of Classification Search .................. 600/101, 600/104, 106, 139, 141, 146, 147, 149, 150, 600/152, 153, 102, 137; 604/510, 528, 95.01, 604/156; 384/453, 454, 455, 490, 491, 492
See application file for complete search history.

(56) References Cited

U.S. PATENT DOCUMENTS

| | | | | | |
|---|---|---|---|---|---|
| 2,036,887 A | * | 4/1936 | Rolfs | ........................ | 242/441.3 |
| 3,625,276 A | * | 12/1971 | Considine et al. | ............ | 164/464 |
| 3,800,580 A | * | 4/1974 | Lewis | ................................ | 72/68 |
| 3,835,854 A | * | 9/1974 | Jewett | ............................ | 604/159 |
| 4,530,507 A | * | 7/1985 | Lee, Jr. | .......................... | 279/151 |
| 5,060,632 A | * | 10/1991 | Hibino et al. | .................. | 600/109 |
| 5,309,746 A | * | 5/1994 | Abbey, III | ........................ | 72/8.3 |
| 5,318,541 A | * | 6/1994 | Viera et al. | .................... | 604/159 |
| 5,346,498 A | * | 9/1994 | Greelis et al. | .................. | 606/108 |
| 5,976,129 A | * | 11/1999 | Desai | ............................... | 606/40 |
| 6,290,675 B1 | * | 9/2001 | Vujanic et al. | ................ | 604/159 |
| 6,358,199 B1 | * | 3/2002 | Pauker et al. | .................. | 600/114 |
| 6,726,675 B1 | * | 4/2004 | Beyar | ............................. | 604/510 |
| 6,849,989 B2 | * | 2/2005 | Schmid et al. | ................ | 310/328 |
| 6,872,178 B2 | * | 3/2005 | Weinberg | ....................... | 600/114 |
| 2003/0040737 A1 | | 2/2003 | Merril et al. | | |

(Continued)

FOREIGN PATENT DOCUMENTS

EP 1 442 720 A1 8/2004

(Continued)

OTHER PUBLICATIONS

Tanii, Yoshiyuki, Endoscope Inserting Device (Machine English Translation), Apr. 18, 2000, PAJ, Drawings pp. 1-4, retrieved from www4.ipdl.inpit.go.jp on Jul. 7, 2010.*

(Continued)

*Primary Examiner* — Linda C Dvorak
*Assistant Examiner* — Alireza Nia
(74) *Attorney, Agent, or Firm* — Scully, Scott, Murphy & Presser, P.C.

(57) ABSTRACT

This endoscopic treatment system is provided with an insertion-retraction and rotating device for a treatment tool, which performs an insertion-retraction operation along a direction of an axis of a treatment tool and a rotating operation around the axis, of the treatment tool inserted in a channel of an endoscope.

5 Claims, 10 Drawing Sheets

U.S. PATENT DOCUMENTS

2004/0034311 A1* 2/2004 Mihalcik .................. 600/585
2005/0171504 A1* 8/2005 Miller .................... 604/506

FOREIGN PATENT DOCUMENTS

| JP | 57-117823 | 7/1982 |
| JP | 9-140663 | 6/1997 |
| JP | 11-104071 | 4/1999 |
| JP | 2000-107123 | 4/2000 |
| JP | 2003-305044 | 10/2003 |
| JP | 2004-016504 | 1/2004 |
| JP | 2004-033787 | 2/2004 |
| WO | WO 99/45994 | 9/1999 |

OTHER PUBLICATIONS

Tanii, Yoshiyuki, Endoscope Inserting Device (Machine English Translation), Apr. 18, 2000, PAJ, Means pp. 1-13, retrieved from www4.ipdl.inpit.go.jp on Jul. 7, 2010.*

Japanese Office Action dated Dec. 15, 2009 with Translation.

* cited by examiner

ENDOSCOPIC TREATMENT SYSTEM

This application is a Continuation Application of International Patent Application No. PCT/JP2005/006777, filed on Apr. 6, 2005, which claims priority from Japanese Patent Application No. 2004-119984, filed on Apr. 15, 2004, the contents of which are incorporated herein.

BACKGROUND OF THE INVENTION

1. Field of the Invention

The present invention relates an endoscopic treatment system.

2. Description of the Related Art

Conventionally, when a treatment tool such as a forceps is inserted into a body cavity through a channel of an endoscope, an operator inserts it into the channel while holding the treatment tool in his own hand. However, for example, since the total length of an endoscope for use with the colon is as long as 2 m, an inserting operation of the treatment tool takes long time, and thereby treatment procedures such as a biopsy become extremely troublesome.

Therefore, in order to reduce the labor, an endoscope provided with an insertion-retraction apparatus that inserts and retracts a treatment tool that is inserted from a treatment tool insertion opening of the endoscope has been proposed (for example, refer to FIG. 1 of Japanese Unexamined Patent Application, First Publication No. S57-117823).

SUMMARY OF THE INVENTION

An endoscopic treatment system according to the present invention is provided with an insertion-retraction and rotating device for a treatment tool, which performs an insertion-retraction operation along a direction of an axis of a treatment tool and a rotating operation around the axis, of the treatment tool inserted in a channel of an endoscope.

The insertion-retraction and rotating device for a treatment tool may include: at least two balls which are to be in contact with the treatment tool; a first driving device which drives rotations of the balls around an axis orthogonal to an insertion-retraction direction of the treatment tool; and a second driving device which drives rotations of the balls around an axis parallel to the insertion-retraction direction of the treatment tool.

The endoscopic treatment system may further include a holding member which holds a contacting portion between the treatment tool and the rollers. An opening which permits contacts between the treatment tool and the rollers may be formed in the holding member.

Each of the rollers may have a disc shape having a length shorter than a radius centering on a rotating axis thereof.

Each of the rollers may make a line contact with respect to the treatment tool.

DETAILED DESCRIPTION OF THE INVENTION

An endoscopic treatment system according to a first embodiment of the present invention will be explained hereinbelow, with reference to FIGS. 1 to 6.

Figure 1:
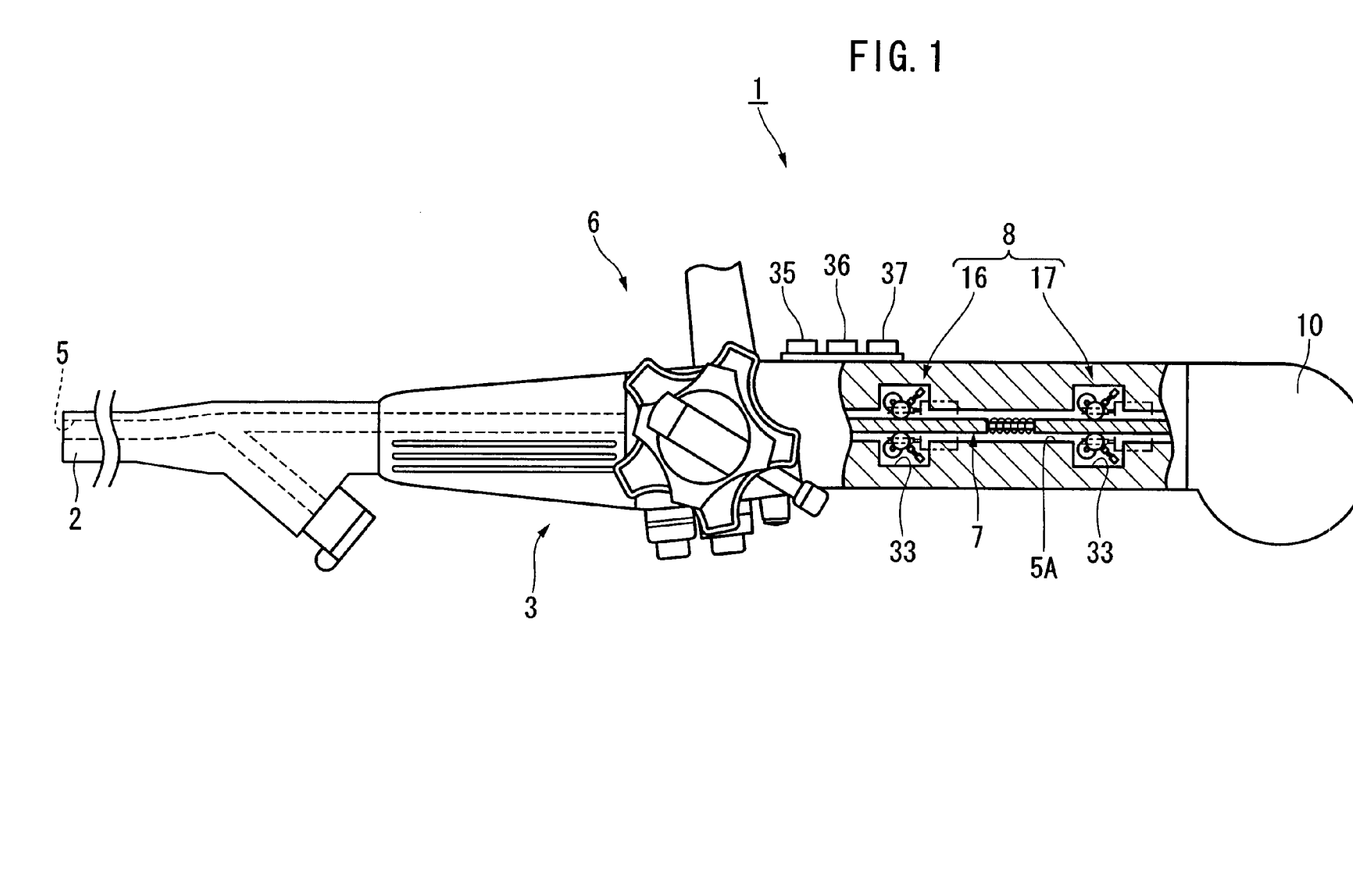
FIG. 1 is a side view showing an endoscopic treatment system according to a first embodiment of the present invention, in which a part thereof is shown in a cross sectional view.

As shown in FIG. 1, an endoscopic treatment system 1 of the present embodiment is provided with: a flexible insertion part 2; an operation part 3 for operating the insertion part 2; an endoscope 6 having a channel 5 communicating between the insides of the insertion part 2 and the operation part 3; a forceps (a treatment tool) 7 to be inserted into the channel 5; and an insertion-retraction and rotating device for a treatment tool 8 which performs insertion-retraction of the forceps 7 in the channel 5, and rotates the forceps 7 centering on the insertion-retraction direction; and an accommodating portion 10 connected to the operating portion 3 and accommodates at least a proximal end side of the forceps 7.

Figure 2:
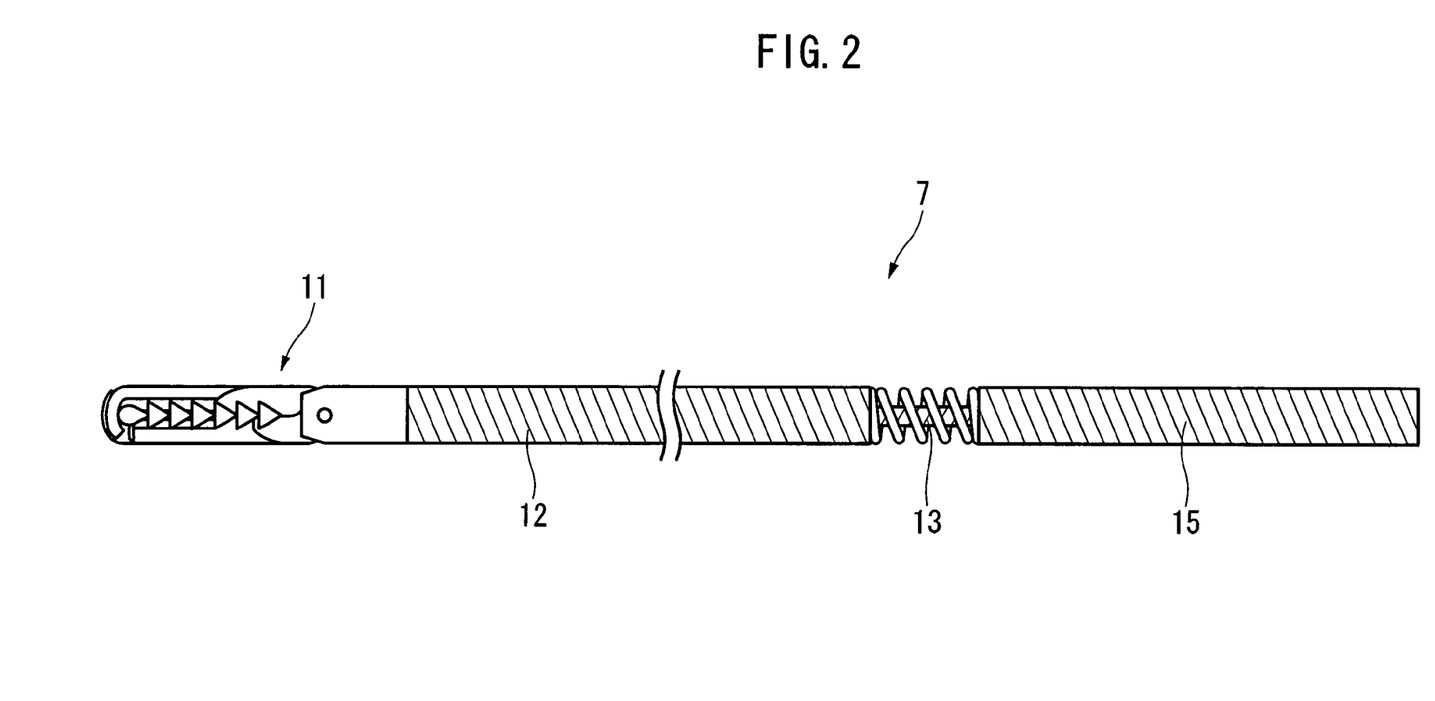
FIG. 2 is a side view showing a treatment tool of the endoscopic treatment system.
Figure 3:
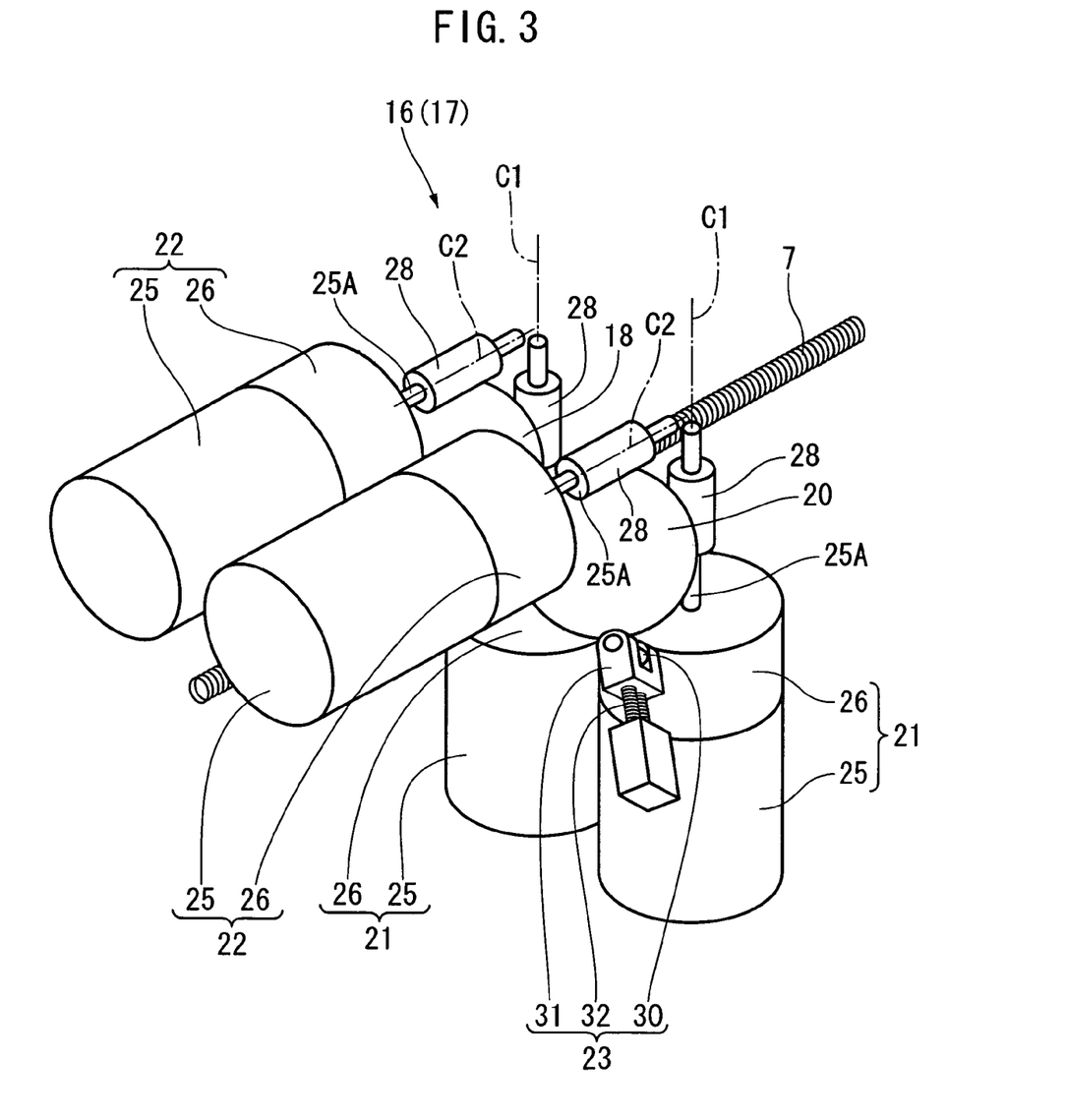
FIG. 3 is a perspective view of an insertion-retraction and rotating device for a treatment tool, of the endoscopic treatment system.
Figure 4:
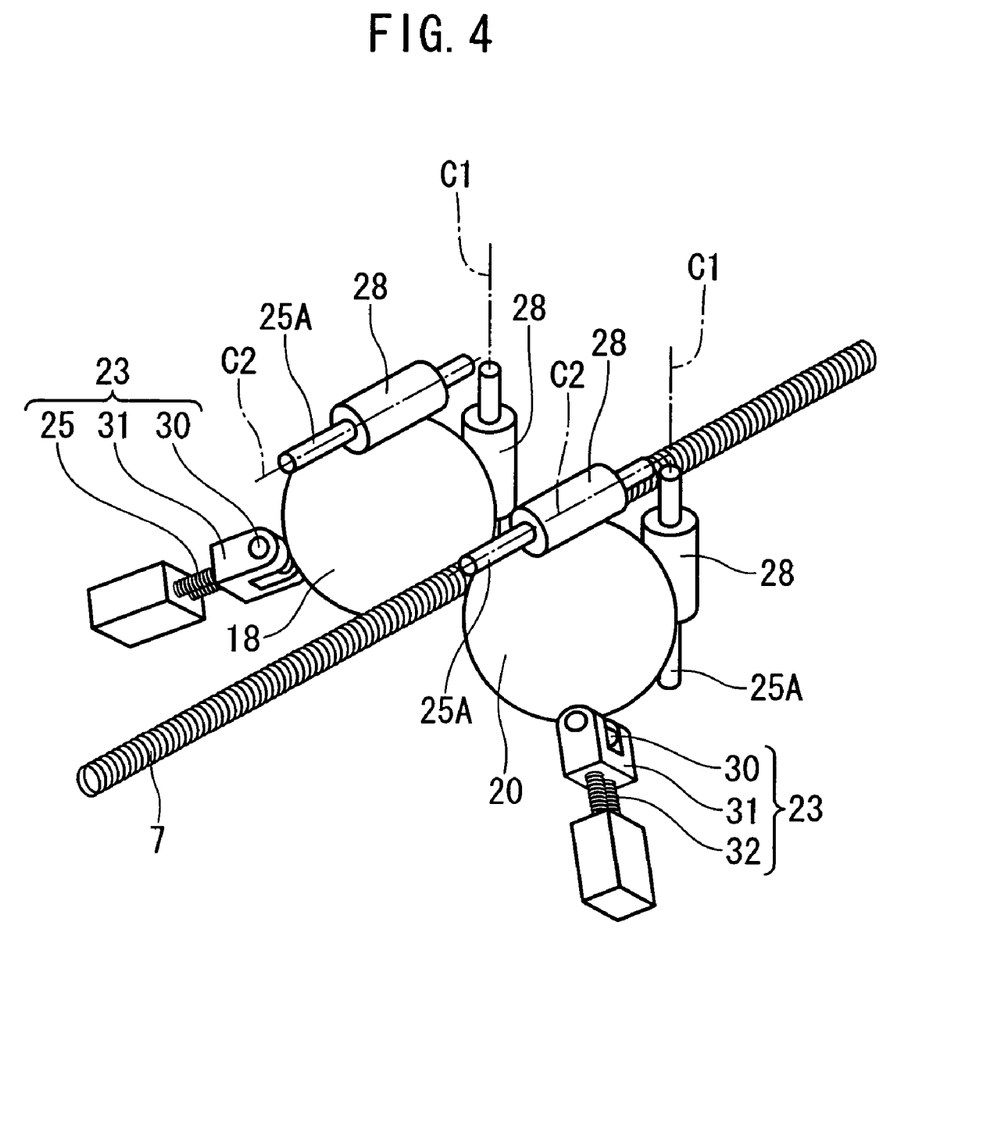
FIG. 4 is a perspective view of a part of the insertion-retraction and rotating device for a treatment tool, of the endoscopic treatment system.
Figure 5:
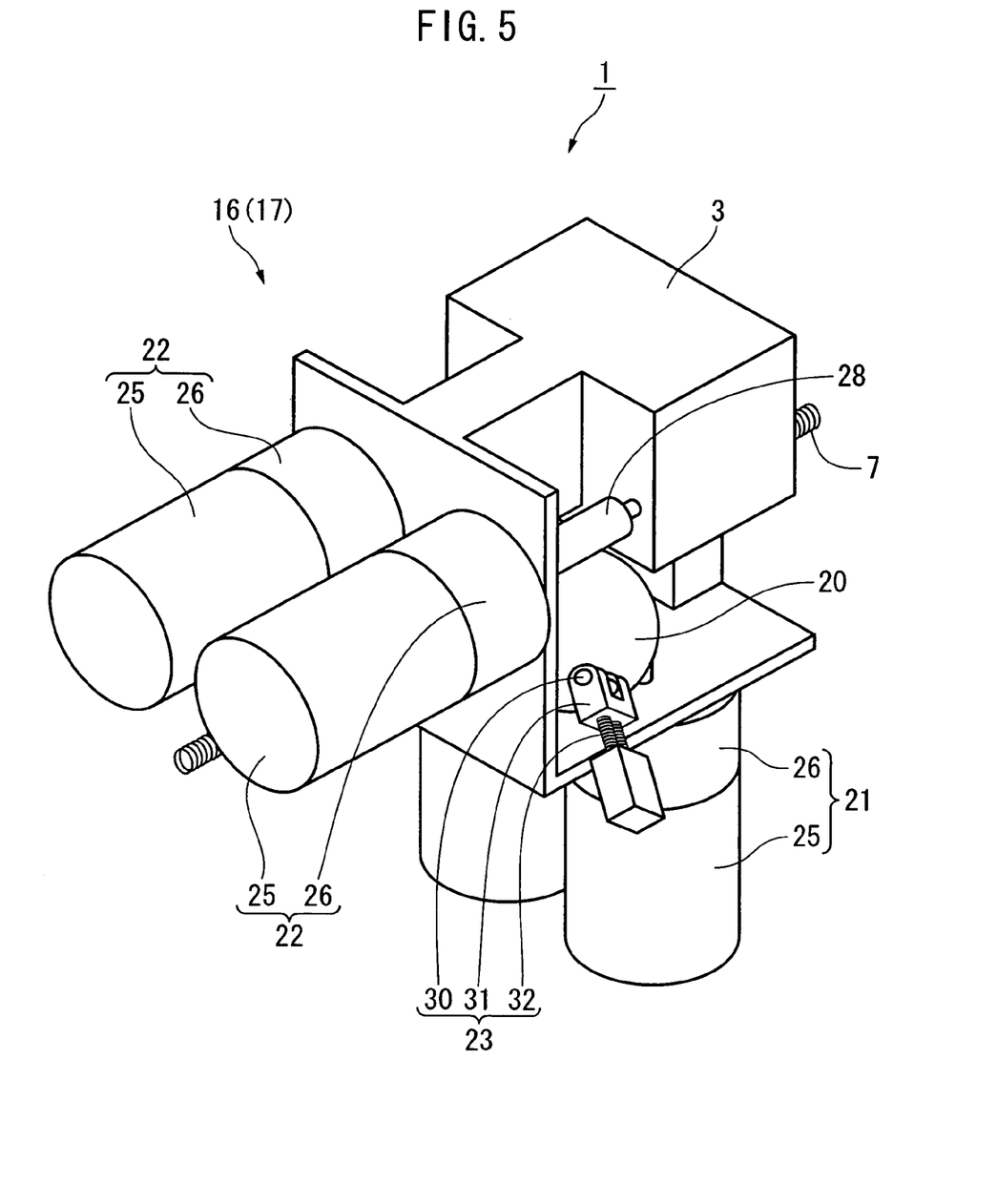
FIG. 5 is a perspective view of a part of the endoscopic treatment system.
Figure 6:
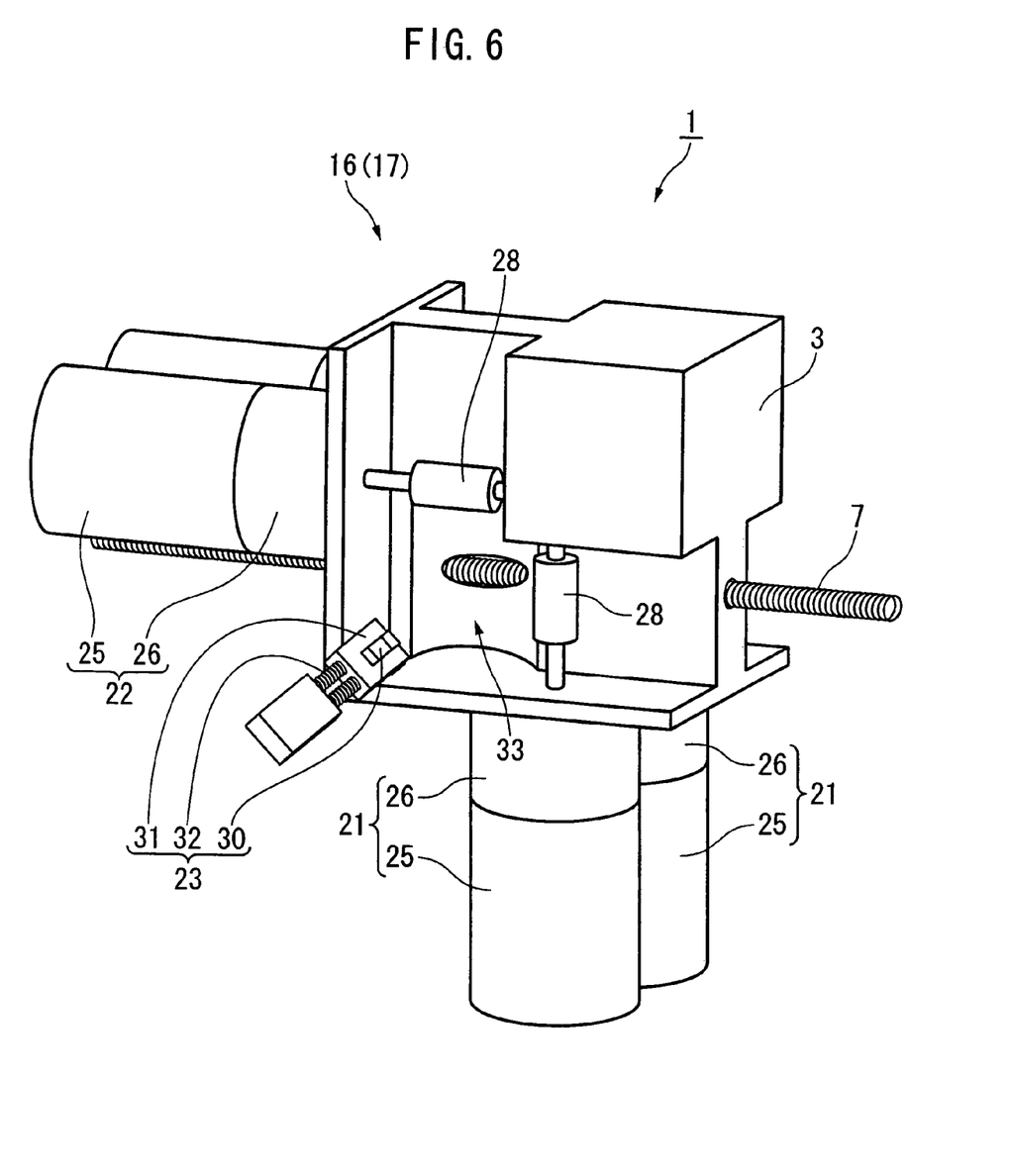
FIG. 6 is a perspective view of a part of the endoscopic treatment system.

As shown in FIG. 2, the forceps 7 is provided with: a forcep portion 11 which opens and closes when an insertion-retraction driving power is applied onto an operation wire 13; a flexible sheath portion 12 having a distal end to which the forcep portion 11 is attached; the operation wire 13 inserted in the sheath portion 12 so as to be insertable and retractable, and transfers the insertion-retraction driving power to the forcep portion 11; and an operation duct portion 15 arranged so as to be separated securing a predetermined length from the proximal end of the sheath portion 12, and is connected to the proximal end of the operation wire 13.

As shown in FIG. 1, the insertion-retraction and rotating device for a treatment tool 8 includes: a distal-end-side insertion-retraction and rotating device for a treatment tool 16 arranged in a passage 5A communicating between the insides of the channel 5 and the accommodating portion 10 within the operating portion 3; and a proximal-end-side insertion-retraction and rotating device for a treatment tool 17 arranged on the retraction side than the distal-end-side insertion-retraction and rotating device for a treatment tool 16 (i.e., on the right side of FIG. 1) so as to be separated therefrom. An interval between the distal-end-side insertion-retraction and rotating device for a treatment tool 16 and the proximal-end-side insertion-retraction and rotating device for a treatment tool 17 is longer than the length of a portion of the forcep portion 11 protruded from the distal end of the channel 5.

As shown in FIGS. 3 to 6, each of the distal-end-side insertion-retraction and rotating device for a treatment tool 16 and the a proximal-end-side insertion-retraction and rotating device for a treatment tool 17 includes: a pair of balls 18 and 20 facing to each other while sandwiching the forceps 7 therebetween; a pair of first driving devices 21 which rotate the balls 18 and 20 around axes parallel to torsion axes C1 vertical to the planar face including the axis of the forceps 7; a pair of second driving devices 22 which rotate the balls 18 and 20 around parallel axes C2 parallel to the insertion-retraction direction of the forceps 7; and a pair of pushing portions 23 which push the balls 18 and 20 toward the forceps 7.

Each of the first driving device 21 and the second driving device 22 is provided with a motor 25, and a gear box 26 accommodating gears for adjusting the rotational number and the torque of the motor 25. Each of rotational axes 25A joined with a rotational axis of the motor 25 via the gears, is joined with a ball roller 28 which extends along the axial direction of the rotational axis 25A and makes a press-contacting with respect to the balls 18 and 20.

Each of the pushing portions 23 is provided with: a pushing roller 30 which contacts one of the balls 18 and 20 and rotates along with the rotation of the ball 18 or 20; a roller supporting portion 31 which supports the roller 30 such that the roller 30 follows the rotational direction of the ball 18 or 20; and a spring portion 32 which urges the roller supporting portion 31 toward the ball 18 or 20.

Each of the pushing portions 23 is arranged at a position where it can press the ball 18 or 20 toward both of the ball roller 28 and the forceps 7.

The balls 18 and 20 are accommodated in each ball-accommodating portion 33 (refer to FIG. 1) of the operation part 3. Each of inner faces of the ball-accommodating portion 33 has a curved shape in accordance with the shape of the balls 18 and 20, such that the balls 18 and 20 can freely rotate at thereinside.

As shown in FIG. 1, an insertion-retraction switch 35 for performing an insertion-retraction operation of the forceps 7 within the channel 5; a rotation switch 36 for a rotation operation of the forceps 7 around the axis thereof; and an open-close switch 37 for opening and closing operations of the forcep portion 11, are arranged at the operation portion 3.

Next, an operation method, and an operation and an advantageous effect of the endoscopic treatment system 1 according to the present embodiment will be explained in the following.

Firstly, the insertion part 2 of the endoscope 6 is inserted into a body cavity.

When performing procedures, the first driving devices 21 of the distal-end-side insertion-retraction and rotating device for a treatment tool 16 and the proximal-end-side insertion-retraction and rotating device for a treatment tool 17 are driven by operating the insertion-retraction switch 35. Then, each of the ball roller 28 contacting the ball 18 and the ball roller 28 contacting the ball 20 is rotated around the torsion axes C1 thereof in the reversed rotational direction with each other and in the same rotational speed.

At this time, each of the balls 18 and 20 rotates in the reversed rotational direction of that of the ball rollers 28, and thereby the forceps 7 pressed by the balls 18 and 20 forwards along the axial direction of the channel 5 and the rotational direction of the balls 18 and 20.

After protruding the forceps 7 for a predetermined length from the distal end of the channel 5, forwarding of the forceps 7 is stopped by operating the insertion-retraction switch 35.

If the rotational direction of the forcep portion 11 and the clamping direction for the tissue differ, the rotation switch 36 is operated. By this, the second driving devices 22 of the distal-end-side insertion-retraction and rotating device for a treatment tool 16 and the proximal-end-side insertion-retraction and rotating device for a treatment tool 17 are each driven. Then, each of the ball roller 28 contacting the ball 18 and the ball roller 28 contacting the ball 20 is rotated around the parallel axes C2 thereof in the reversed rotational direction with each other and in the same rotational speed.

As a result, each of the balls 18 and 20 rotates in the reversed rotational direction of that of the ball rollers 28, and thereby the forceps 7 pushed by the balls 18 and 20 rotates around the rotational axis thereof along the rotational direction of the balls 18 and 20.

While performing the procedures, only the first driving device 21 on the proximal-end-side insertion-retraction and rotating device for a treatment tool 17 side is activated by operating the open-close switch 37. Then, each of the ball rollers 28 on the proximal-end-side insertion-retraction and rotating device for a treatment tool 17 side is driven to rotate in the forward direction in which the forceps 7 moves toward the distal end of the channel 5.

At this time, since both of the operation duct portion 15 and the operation wire 13 move in the forward direction with respect to the sheath portion 12, driving power is transmitted to the forcep portion 11, and thereby enabling driving of the forcep portion 11.

After the procedures, the first driving devices 21 of the distal-end-side insertion-retraction and rotating device for a treatment tool 16 and the proximal-end-side insertion-retraction and rotating device for a treatment tool 17 are driven such that the balls 18 and 20 rotate in the reversed direction with respect to the above-mentioned direction, by operating the insertion-retraction switch 35. As a result, the forceps 7 is retracted.

According to the above-mentioned endoscopic treatment system 1 of the present embodiment, the forceps 7 can be moved along the rotational direction of the balls 18 and 20 by driving the first driving device 21 while the balls 18 and 20 contact the forceps 7. Furthermore, the insertion-retraction direction of the forceps 7 can also be operated by rotating the balls 18 and 20 in the normal rotational direction or in the reversed rotational direction.

In addition, the forceps 7 can be moved along the rotational direction of the balls 18 and 20 by driving the second driving device 22. Furthermore, the rotational direction of the forceps 7 around the axis thereof can also be operated by rotating the balls 18 and 20 in the normal rotational direction or in the reversed rotational direction.

Next, an endoscopic treatment system 40 according to a second embodiment of the present invention will be explained in the following with reference to FIGS. 7 to 11. Moreover, the same symbols will be applied onto the same constituent elements as those of the above-mentioned first embodiment, and the explanation therefor will be omitted.

Figure 7:
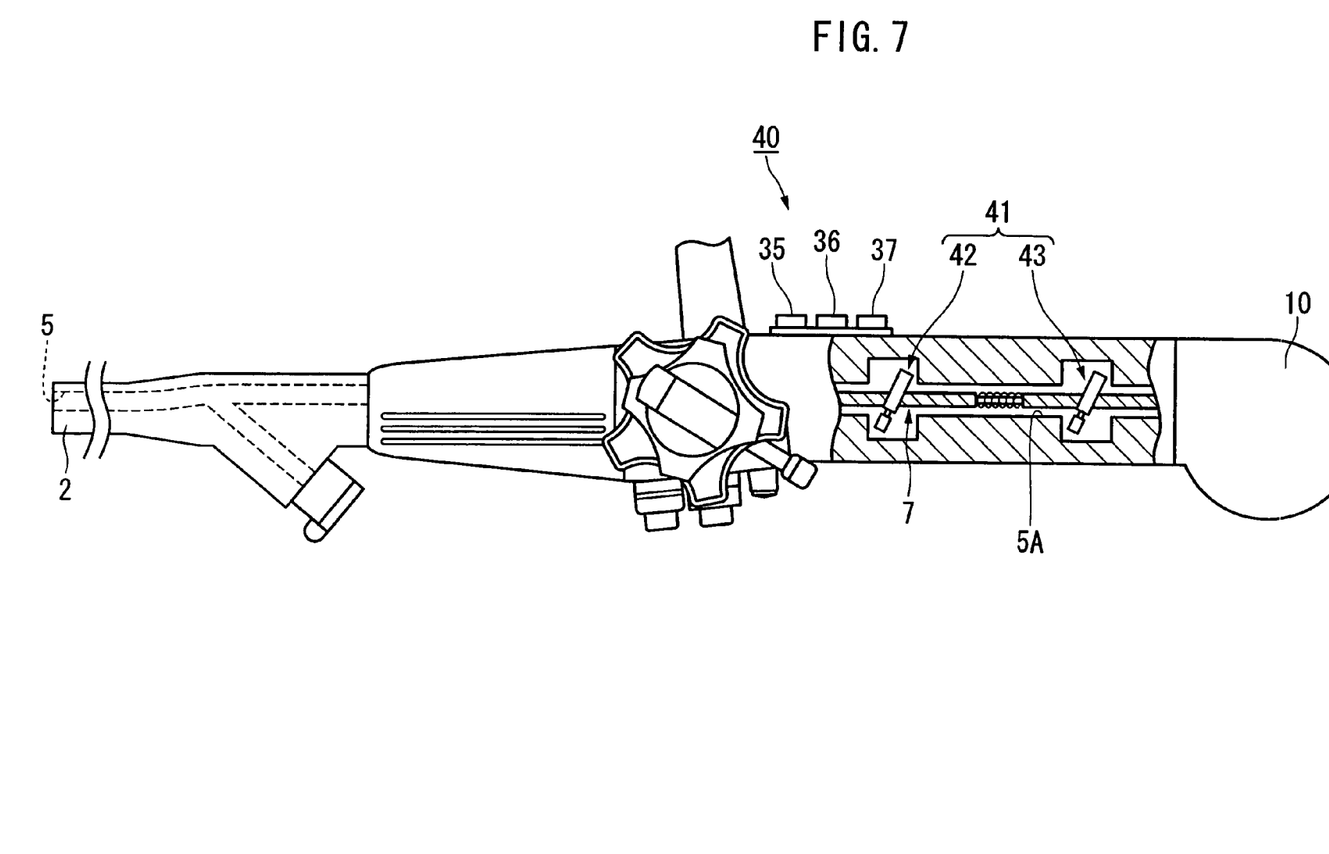
FIG. 7 is a side view showing an endoscopic treatment system according to a second embodiment of the present invention, in which a part thereof is shown in a cross sectional view.
Figure 8:
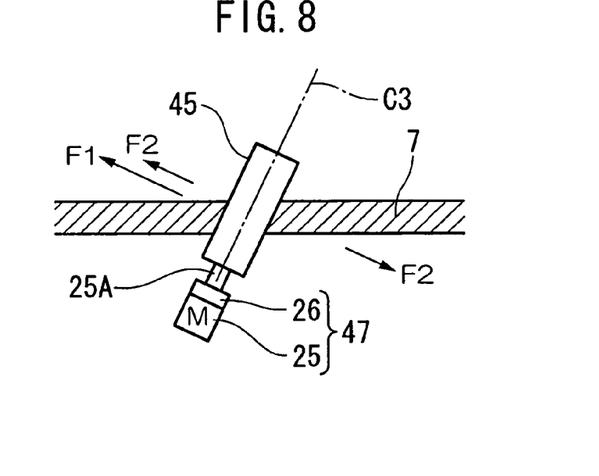
FIG. 8 is a side view of a part of the endoscopic treatment system.
Figure 9:
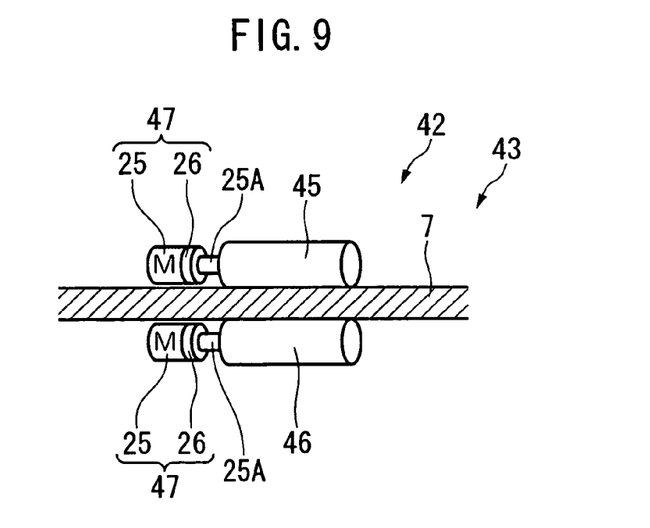
FIG. 9 is a plan view of the part of the endoscopic treatment system.

The endoscopic treatment system 40 of the present embodiment differs with the endoscopic treatment system 1 of the first embodiment in the point in that a distal end side insertion-retraction and rotating device for a treatment tool 42 and a proximal end side insertion-retraction and rotating device for a treatment tool 43 of an insertion-retraction and rotating device for a treatment tool 41 is provided with, as shown in FIGS. 7 to 9, two rollers 45 and 46 sandwiching and pushing the forceps 7 therebetween, and two driving devices 47 which rotationally drive these rollers 45 and 46 around torsion axes C3 which cross with respect to the insertion-retraction direction with an angle of substantially 45 degrees.

Each of the driving devices 47 includes a motor 25, and a gear box 26 accommodating gears for adjusting the rotational number and the torque of the motor 25. Each of the two rollers 45 and 46 is joined with a rotational axis 25A which is joined with a rotational axis of the motor 25 via the gears.

Figure 10:
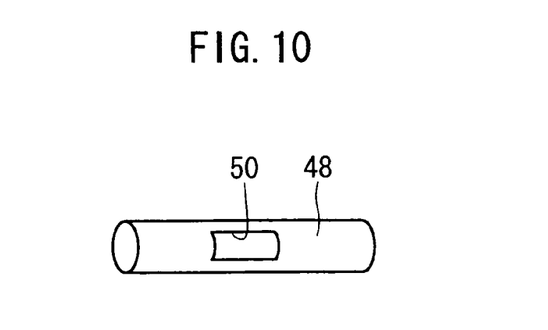
FIG. 10 is a perspective view of a holding member of the endoscopic treatment system.
Figure 11:
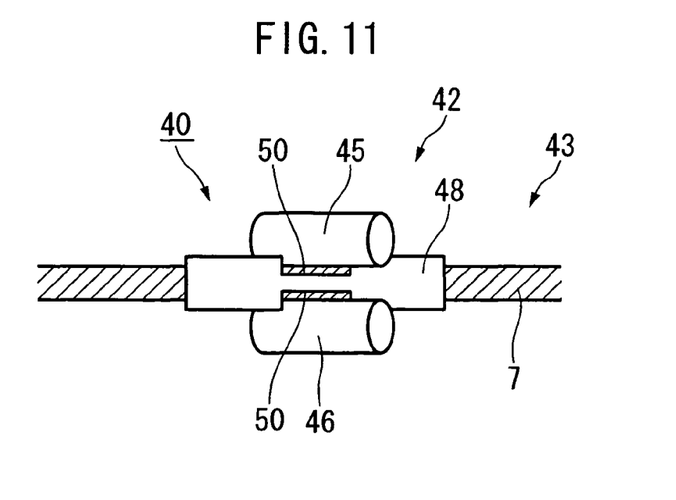
FIG. 11 is a side view of a part of the endoscopic treatment system.

Each of the rollers 45 and 46 has a rod-shape which extends along the torsion axis C3. Moreover, although omitted in FIGS. 8 and 9, as shown in FIG. 10, a holding member 48 which holds a contacting portion between the rollers 45 and 46 and the forceps 7 is arranged at a position where the rollers 45 and 46 and the forceps 7 contact with each other. This holding member 48 holds the forceps 7 which passes through thereinside such that the forceps 7 is insertable and retractable along the axial direction of the forceps 7 and such that the forceps 7 is rotatable around the axis of the forceps 7. As shown in FIG. 11, a pair of slits 50 are formed on an exterior of the holding member 48 so as to extend along the axial direction of the holding member 48. The rollers 45 and 46 contact and push the forceps 7 inside the holding member 48 through the slits 50.

Next, an operation method, and an operation and an advantageous effect of the endoscopic treatment system 40 will be explained in the following.

Firstly, the insertion part 2 is inserted into a body cavity. When performing procedures, the rollers 45 and 46 are rotated at the same rotational speed in the opposite rotational directions with each other (If it is explained using FIG. 9, the roller 45 is rotated in the clockwise while the roller 46 is rotated in the anticlockwise), by operating the insertion-retraction switch 35. At this time, as shown in FIG. 8, a force F1 which is orthogonal to the torsion axis C3 and has the same rotational direction as that of the torsion axis C3 is applied onto the forceps 7. Since the forceps 7 is supported by the holding member 48, only a component taking along the axial direction of the forceps 7, of the force F1 works on the forceps 7; thereby, the forceps 7 moves along the axial direction thereof.

If the rotational direction of the forcep portion 11 and the clamping direction of the tissue differ, the rollers 45 and 46 are rotated in the same rotational direction and the same rotational speed by operating the rotation switch 36. Then, forces F2 which are orthogonal to the torsion axis C3 and have the opposite rotational direction with each other are applied onto the forceps 7. Since the forceps 7 is supported by the holding member 48, components taking along the axial direction of the forceps 7, of the forces F2 are cancelled with each other; therefore, only components which provide a rotational torque onto the forceps 7 works onto the forceps 7 and rotates the forceps 7 around the axis thereof.

In the case in which the forceps 7 needs to be rotated in the opposite direction as of the above-mentioned rotational direction, the rollers 45 and 46 are rotated in the opposite rotational direction as of the above-mentioned rotational direction. As a result, as same as the above-mentioned operation, the forceps 7 rotates around the axis thereof (However, the rotational direction thereof is opposite with respect to the above-mentioned rotational direction).

According to the above-mentioned endoscopic treatment system 40 of the present embodiment, by driving rotations of the rollers 45 and 46 by the driving device 47 while sandwiching the forceps 7 between the rollers 45 and 46, it is possible to generate force having a component taking along the insertion-retraction direction of the forceps 7 and a component orthogonal to the insertion-retraction direction of the forceps 7, toward the direction orthogonal to the torsion axis C1. In this case, by making the rollers 45 and 46 rotate in the opposite rotational directions with each other, the forceps 7 can be inserted and retracted within the channel 5. In addition, by making the rollers 45 and 46 rotate in the same rotational direction, the forceps 7 can be rotated around the axis thereof.

Figure 12:
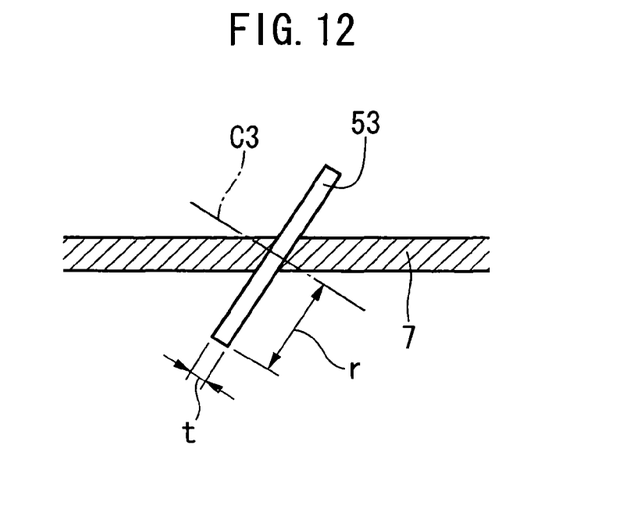
FIG. 12 is a side view showing a part of an endoscopic treatment system according to a third embodiment of the present invention.
Figure 13:
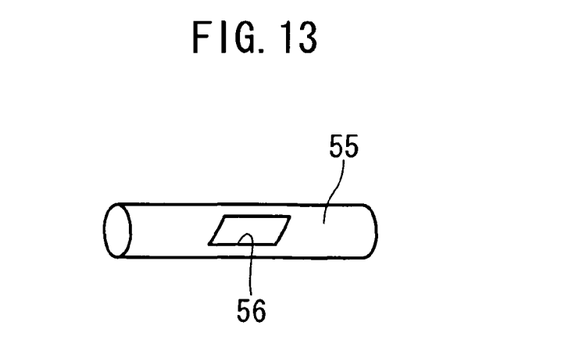
FIG. 13 is a perspective view of a holding member of the endoscopic treatment system.
Figure 14:
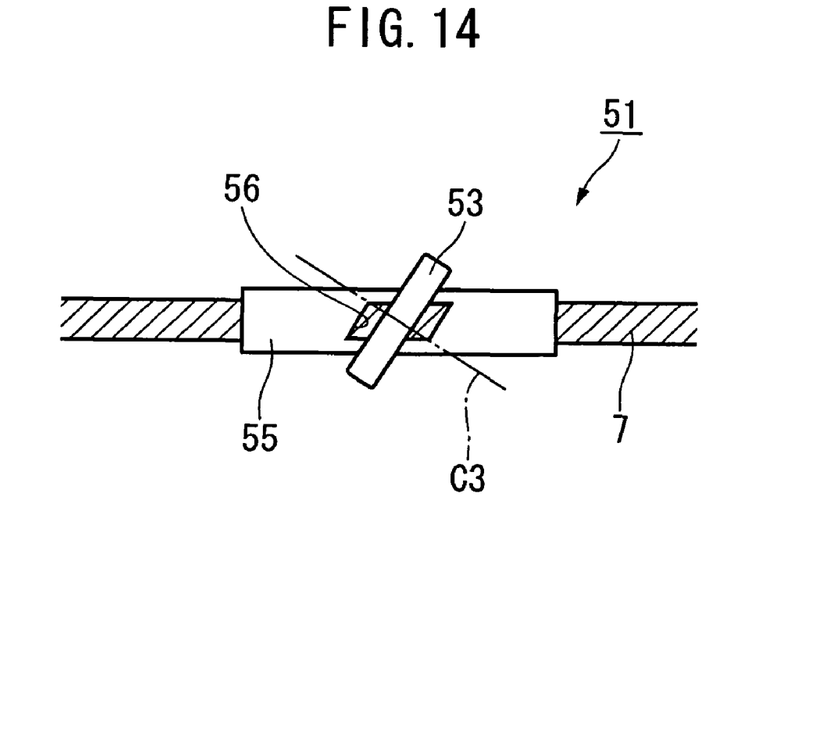
FIG. 14 is a side view of a part of the endoscopic treatment system.

Next, an endoscopic treatment system 51 according to a third embodiment of the present invention will be explained in the following with reference to FIGS. 12 to 14. Moreover, the same symbols will be applied onto the same constituent elements as those of the above-mentioned other embodiments, and the explanation therefor will be omitted.

The endoscopic treatment system 51 of the present embodiment differs with the endoscopic treatment system 40 of the second embodiment in the point in that rollers 53 having flat-shape (disc-shape) in which a radius r centering on the torsion axis C3 is longer than the length t taking along the axial direction of the torsion axis C3.

Slits 56 provided in a holding member 55 are formed in an inclined direction with respect to the rotational axis of the forceps 7 such that the rollers 53 and the forceps 7 contact with each other.

The endoscopic treatment system 51 can also obtain the same operations and advantageous effect as those of the endoscopic treatment system 40 according to the above-mentioned second embodiment. Furthermore, the endoscopic treatment system 51 of the present embodiment can obtain a smaller contacting area between the forceps 7 and the rollers 53; thereby, enabling reducing friction forces between the rollers 53 and the forceps 7. Accordingly, force from the rollers 53 can be efficiently transferred to the forceps 7.

Figure 15:
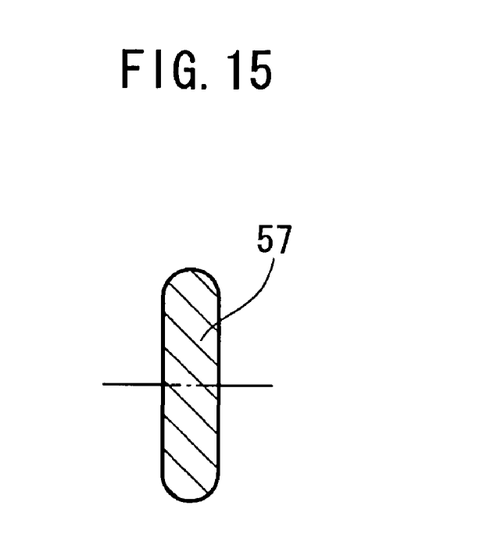
FIG. 15 is a cross sectional view of a roller of a variant example of the endoscopic treatment system.

Moreover, in the present embodiment, contacting faces of the rollers 53 with respect to the forceps 7 are made planar; however, as shown in for example FIG. 15, rollers 57 each having a round-shaped contacting surface which makes a line contact with the forceps in order to further reduce the contacting area with respect to the forceps 7 may be adopted. In this case, pushing force of the rollers 57 toward the forceps 7 can be increased; thereby, enabling efficient transmission of the rotations of the rollers 57 to the forceps 7.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

The endoscopic treatment system according to the present invention described in the above will be summarized hereinbelow.

The endoscopic treatment system according to the present invention is provided with an insertion-retraction and rotating device for a treatment tool, which performs an insertion-retraction operation along a direction of an axis of a treatment tool and a rotating operation around the axis, of the treatment tool inserted in a channel of an endoscope.

According to the endoscopic treatment system, by driving the insertion-retraction and rotating device for a treatment tool, not only an insertion-retraction of the treatment tool inserted in the channel, but also a rotation of the treatment tool around the insertion-retraction direction becomes possible. Therefore, even when using a long treatment tool which requires difficult operations, an insertion-retraction operation can be made easily. Furthermore, a direction of the treatment tool can be changed easily.

Thus, according to the endoscopic treatment system, by automatically performing the insertion-retraction operation and rotating operation, it becomes possible to perform manual procedure using the treatment tool in shorter time.

The insertion-retraction and rotating device for a treatment tool may include: at least two balls which are to be in contact with the treatment tool; a first driving device which drives rotations of the balls around an axis orthogonal to an insertion-retraction direction of the treatment tool; and a second driving device which drives rotations of the balls around an axis parallel to the insertion-retraction direction of the treatment tool.

In this case, when the first driving device is driven while the balls contact with the treatment tool, driving power is generated for moving the treatment tool in accordance with the rotational direction of the balls. The treatment tool can be inserted and retracted, since the driving power includes power component taking along the insertion-retraction direction of the treatment tool. In addition, when the second driving device is driven, driving power can be generated for moving the treatment tool in accordance with the rotational direction of the balls. The treatment tool can be rotated around an axis thereof, since the driving power includes power component orthogonal to the insertion-retraction direction of the treatment tool.

The insertion-retraction and rotating device for a treatment tool may include: at least two rollers which are to be in contact with the treatment tool; and a driving device which drives rotations of the rollers around an axis inclined with respect to a planar face orthogonal to the insertion-retraction direction of the treatment tool.

In this case, when the driving device rotationally drives the rollers contacting with the treatment tool, it becomes possible to generate driving power including power component taking along the insertion-retraction direction of the treatment tool and power component orthogonal to the insertion-retraction direction, toward a direction orthogonal to axes of the rollers. At this time, since at lest two rollers are provided, by the combination of the rotational directions of the rollers, it is possible to perform insertion-retraction of the treatment tool along the axis thereof and rotation of the treatment tool around the axis thereof.

What is claimed is:

1. An endoscopic treatment system comprising an insertion-retraction and rotating device for a treatment tool, which performs an insertion-retraction operation along an insertion-retraction direction of a longitudinal axis of a treatment tool and a rotating operation around the longitudinal axis, of the treatment tool inserted in a channel of an endoscope, wherein
the insertion-retraction and rotating device for a treatment tool comprises:
a pair of rollers which are to be directly in contact with the treatment tool;
a driving device which drives rotations of the pair of rollers in rotational directions around respective axes thereof which are parallel to each other; and
a holding member which is disposed between the treatment tool and the pair of rollers and holds a contacting portion between the treatment tool and the pair of rollers, wherein
said pair of rollers are inclined with respect to the insertion-retraction direction of the treatment tool and to a planar face orthogonal to the insertion-retraction direction of the treatment tool,
an opening which permits contacts between the treatment tool and said pair of rollers is formed in the holding member; and
the insertion-retraction operation and the rotating operation of the treatment tool can be performed by varying combination of the rotational directions of said pair of rollers.

2. The endoscopic treatment system according to claim 1, wherein each of the pair of rollers has a disc shape having a thickness smaller than a radius centering on a rotating axis thereof.

3. The endoscopic treatment system according to claim 2, further comprising a holding member which holds a contacting portion between the treatment tool and the pair of rollers, wherein
an opening which permits contacts between the treatment tool and the rollers is formed in the holding member.

4. The endoscopic treatment system according to claim 1, wherein each of the pair of rollers makes a line contact with respect to the treatment tool.

5. An endoscopic treatment system according to claim 1, wherein said driving device performs said insertion-retraction operation by rotating one of said pair of rollers in a direction opposite with a rotational direction of another of said pair of rollers, and performs the rotating operation by rotating one of said pair of rollers and another of said pair of rollers in the same rotational direction.

\* \* \* \* \*